United States Patent [19]

Triplett et al.

[11] 4,256,727

[45] Mar. 17, 1981

[54] SYNTHESIS AND USE OF DIAGNOSTIC RADIO-PHARMACEUTICALS COMPRISING RADIOACTIVE ISOTOPES OF BROMINE WITH DYES

[75] Inventors: John W. Triplett; Randall B. Smith, both of Lexington, Ky.

[73] Assignee: The University of Kentucky Research Foundation, Lexington, Ky.

[21] Appl. No.: 943,555

[22] Filed: Sep. 18, 1978

[51] Int. Cl.³ .................. A61K 49/00; A61K 43/00; G01T 33/48; G01T 1/00
[52] U.S. Cl. ................................ 424/1.5; 260/343.4; 260/335; 424/1; 424/9; 549/33
[58] Field of Search ................ 424/1, 1.5, 9; 260/343.4, 335; 549/33

[56] References Cited

U.S. PATENT DOCUMENTS

| | | |
|---|---|---|
| 2,772,290 | 11/1956 | Vodak et al. ............................ 549/33 |
| 3,673,410 | 6/1972 | Waite et al. ............................ 424/1.5 |
| 3,743,713 | 7/1973 | Kato et al. ........................... 260/343.4 |
| 3,872,046 | 3/1975 | Torii et al. .............................. 549/33 |
| 3,959,455 | 5/1976 | Ansari et al. .............................. 424/1 |

*Primary Examiner*—Brooks H. Hunt
*Assistant Examiner*—Christine M. Nucker
*Attorney, Agent, or Firm*—Birch, Stewart, Kolasch & Birch

[57] ABSTRACT

A process for preparing bromine-containing dyes labelled with gamma-emitting isotopes of bromine, and the product thereof which is useful as an imaging agent for the hepato-biliary system, particularly in dynamic imaging methods. The dyes prepared are from the class of triarylmethane dyes, and also from the phthalein subclass of the class of xanthene dyes, and the labelling thereof is effected with $^{76}$Br, $^{77}$Br or $^{82}$Br. The process for preparing these dyes involves reacting the non-brominated dye precursor with either $^{76}$Br$_2$, $^{77}$Br$_2$ or $^{82}$Br$_2$. This is a substitution type of reaction in which a ring hydrogen is substituted by either $^{76}$Br, $^{77}$Br or $^{82}$Br.

11 Claims, 2 Drawing Figures

SYNTHESIS AND USE OF DIAGNOSTIC RADIO-PHARMACEUTICALS COMPRISING RADIOACTIVE ISOTOPES OF BROMINE WITH DYES

FIELD OF THE INVENTION

This invention relates to a process for making bromine-containing dyes labelled with gamma-emitting isotopes of bromine, and the product thereof which is useful as a diagnostic radio-pharmaceutical. More particularly, the invention is concerned with the procedure employed for synthesizing said dyes labelled with gamma-emitting isotopes of bromine, which involves precautions for minimizing the exposure of personnel to damaging levels of harmful radiation. Also, the invention is particularly concerned with the use of a diagnostic radiopharmaceutical product which is far superior to presently known products employed in diagnostic nuclear medicine as imaging agents for the hepato-biliary system to visualize abnormalities and to determine the function thereof by dynamic imaging.

THE PRIOR ART

Related Diagnostic Radiopharmaceutical Products Of The Prior Art Which Are Useful As Imaging Agents For The Hepato-biliary System The drug which has been most widely used in the diagnosis of liver malfunction and measurement of hepato-biliary function in nuclear medicine is a radioactive dye, i.e., Rose Bengal in which the iodine substituents are of the $^{131}$I type. This dye is prepared in high yield by an exchange reaction. The procedure involves refluxing Rose Bengal in acid form with radio-iodine (Na*I and oxidizing agent) overnight to carry out an exchange type of reaction. The radioiodinated Rose Bengal acid is precipitated with acid, washed with water, and, by treatment with sodium hydroxide, is formulated as the sodium salt. This material can then be sterilized by autoclaving or sterile filtration. The product is stable when formulated with propylene glycol and stored at refrigerated temperatures.

Another drug suggested as a potential hepato-biliary imaging agent is dibromo-estrone, in which the bromine substituents are $^{77}$Br. Spicer et al, *Int. J. Appl. Rad. 2nd Isot.*, Vol. 28, pp. 163–168 (1977) have suggested that $^{77}$Br-2,4-dibromoestrone may be a tracer of potential value for liver and gallbladder function studies.

U.S. Pat. No. 3,928,552 to Winchell et al, issued Dec. 23, 1975, is directed to a radiopharmaceutical comprising 2-mercaptoisobutyric acid chelating reduced technetium-99m for scintigraphically imaging the liver and biliary tract morphology and function.

U.S. Pat. No. 3,981,980 to Baker et al, issued Sept. 21, 1976, is directed to a diagnostic substance for cholescintigraphy which is formed by the reaction of pyridoxal and amino acids labelled with a radionuclide, in pyrogen-free water, the reaction product being adjusted to a pH of 8 to 9 and then autoclaved and cooled to produce a sterile, pyrogen-free non-antegenic solution for injection for biliary scanning.

Comparison With Presently Employed Products Used In Diagnosis Of Liver Function And Measurement of Hepato-biliary Function In Nuclear Medicine As noted above, the drug most widely used in the diagnosis of liver malfunction and measurement of hepato-biliary function in nuclear medicine today is Rose Bengal-$^{131}$I. This particular isotope, because of the emission of particulate matter ($\beta^-$), is not ideally suited for use in humans. The consequences of the use of $\beta^-$ emitting radiopharmaceuticals include:

(a) The dose must be very low;
(b) Preparations which contain excessive $^{131}$I as the iodide can endanger the thyroid because iodide is concentrated in this organ;
(c) The drug is cleared from the blood at a relatively slow rate (8–10 min. half life for Rose Bengal compared with 1.5 min. for bromphenol blue).

The rate of blood clearance becomes important in considering the length of time one must wait after injection prior to imaging.

There is an alternative iodine label (Iodine-123) which like bromine-77 is cyclotron produced. This isotope does not decay by emission of particulate matter, but has a single $\gamma$ ray of 0.16 Mev. The major drawback is that iodine-123 has a short half life (13 hours). This limitation in half life would necessitate the in-house production of radiopharmaceuticals labelled with iodine-123; this limits its use to facilities which are physically close to a cyclotron. Bromine-77, however, due to its relatively long half life (56 hours) can be produced at the cyclotron site, incorporated into a radiopharmaceutical, shipped anywhere in the country, and stored for several days before use.

An alternative method for estimating hepato-biliary function is the use of contrast agents and X-rays. In this type of diagnostic procedure, the patient ingests a large dose (600 mg) of drug and after 12 hours undergoes exposure to an external source of radiation. The disadvantages of this procedure are:

(a) Large dose of drug; the contrast agents are known to have specific toxicosis;
(b) The patient receives a much larger dose of radiation (a single X-ray exposes the patient to a greater dose than the total exposure of the radioactive dye);
(c) The diagnosing physician gets much less information to work with.

For example, the X-ray procedure gives one or two points in time, while the nuclear medicine technique can give dynamic data involving literally thousands of data points over a period of time. It should be re-emphasized that the radiation technique exposes the patient to a much higher dose of radiation for one data point than the nuclear medicine technique does for thousands of data points.

OBJECTS OF THE INVENTION

An object of the present invention is to provide a process for producing a diagnostic radiopharmaceutical product labelled with a radioactive halogen by a substitution type of reaction not previously employed in the prior art, and which is simpler to carry out than the prior art processes involving exchange reactions.

Another object of the present invention is to provide a diagnostic radiopharmaceutical product labelled with a radioactive halogen which does not have the disadvantages of the products previously employed in the prior art for hepatic-biliary morphology and function studies.

A further object of the invention is to provide a method for using the diagnostic radiopharmaceutical product of the invention in nuclear medicine techniques.

These and other objects and advantages of the present invention will become apparent to those skilled in the art from a consideration of the following specification and claims, taken in conjunction with the accompanying drawings.

GENERAL DESCRIPTION OF THE INVENTION

The starting material is the immediate precursor of the finally desired dye containing no bromine. For example, if the finally desired dye is tetrabromophenolphthalein in which the four bromine atoms are either $^{76}Br$, $^{77}Br$ or $^{82}Br$, then the starting material is the well known phenolphthalein. The finally desired dye must of course be already known to be one which is excreted to a large extent in bile in a number of animal species. The synthesis occurs through the reaction of $^{76}Br_2$, $^{77}Br_2$ or $^{82}Br_2$ in glacial acetic acid or any other suitable inert reaction medium with said immediate precursor of the dye containing no bromine. The radioactive product is recovered from the reaction mixture by evaporation of the reaction medium containing it, separated by selective extraction, and purified by column chromotography or other suitable procedure.

DETAILED DESCRIPTION OF THE INVENTION

Figure 1:
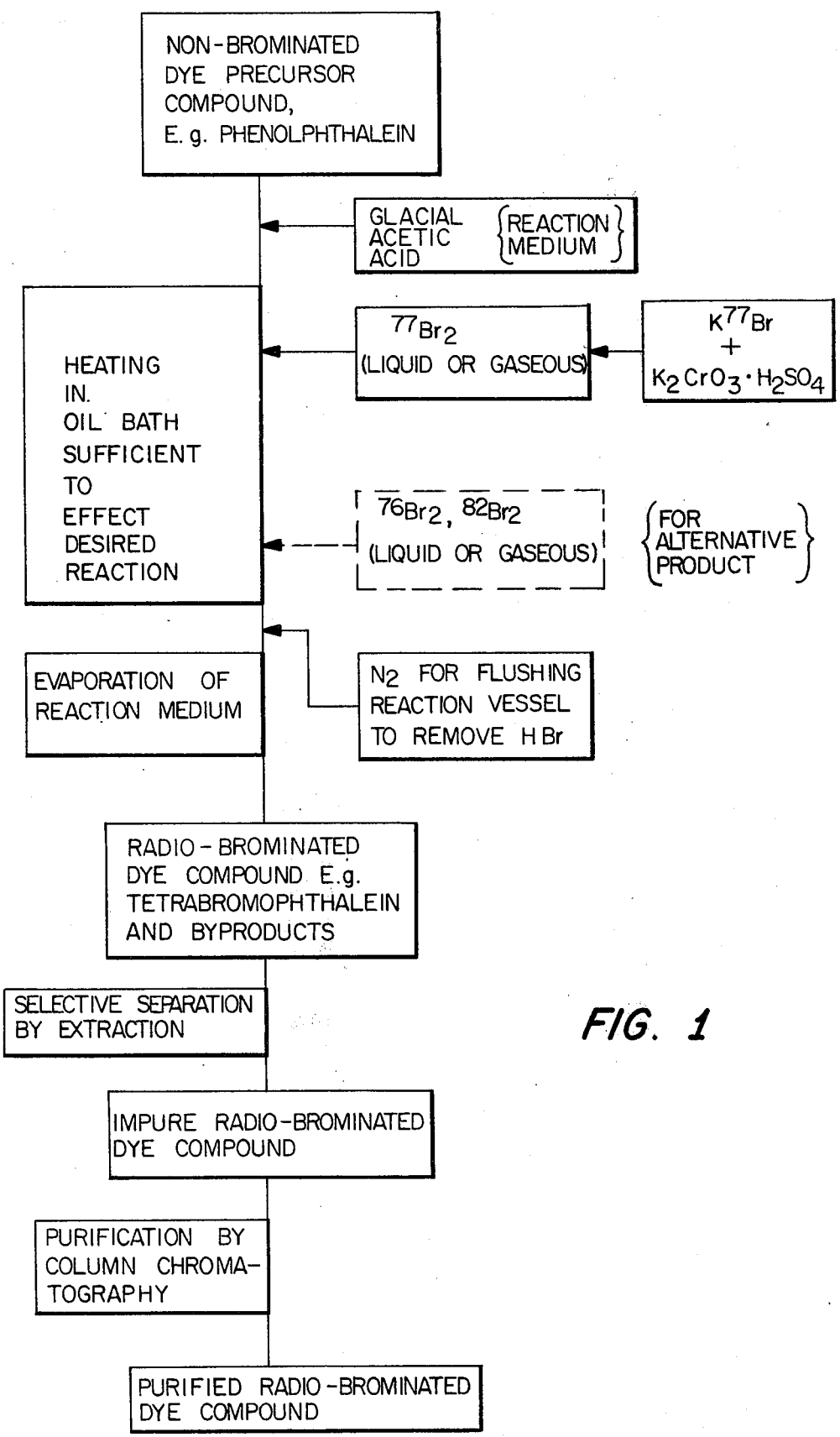

A more complete understanding of the procedures and products of the present invention may be had by reference to the accompanying drawings in which FIG. 1 is a schematic flow diagram of the processes of the invention setting forth the preferred modes of operation.

Figure 2:
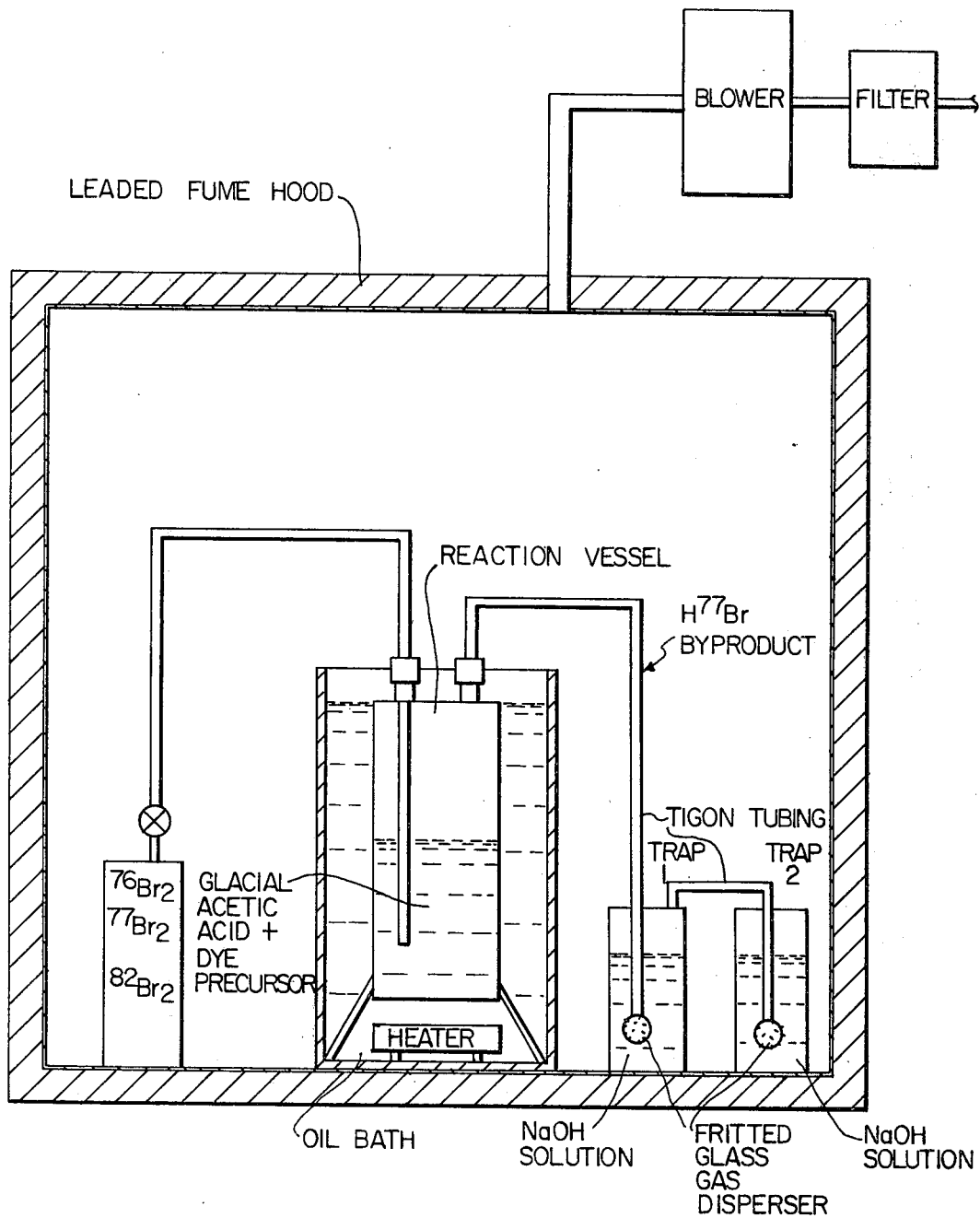

FIG. 2 illustrates an apparatus suitable for carrying out the process shown in FIG. 1.

The flow diagram of FIG. 1 mentions certain specific reactants and procedural steps which are the most desirable in carrying out the present invention. Other reactants and procedural steps can be employed, however, as will be explained more fully in a later section of this specification. For instance, although the flow diagram refers specifically to the use of $^{76}Br_2$, $^{77}Br_2$ or $^{82}Br_2$ as the brominating agent for the dye precursor compound, the use of other gamma-emitting isotopes of $Br_2$ is feasible.

In the starting stage of this flow diagram there is given, as an example of a suitable dye precursor compound, phenolphthalein. All of the dyes in the following Table can be prepared by the process of this invention. They are shown in their final brominated form, including tetrabromophthalein. The starting compounds are, of course, the same as the final dye compounds except that they are not brominated in any position.

TABLE I

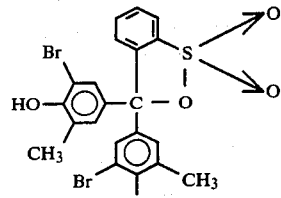

(1) Bromphenol Blue: 4,4'-(3H-2,1,-benzoxathiol-3-ylidene)bis[2,6-dibromophenol]S,S,-dioxide

TABLE I-continued

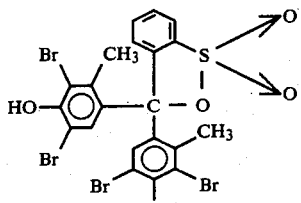

(2) Bromcresol purple: 4,4'-(3H-2,1-benzoxathiol-3-ylidene)bis[2-bromo-6-methylphenol]S,S-dioxide

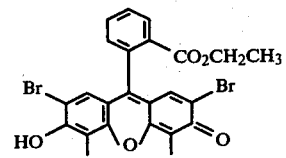

(3) Bromcresol green: 4,4'-(3H-2,1-benzoxathiol-3-ylidene)bis[2,6-dibromo-3-methylphenol]S,S-dioxide

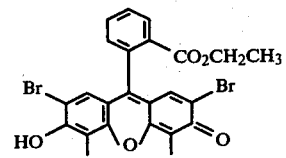

(4) Ethyl Eosin: 2',4',5',7',-tetrabromofluorescein ethyl ester

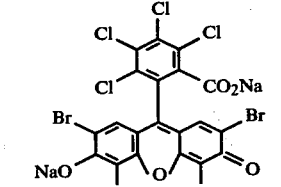

(5) Philoxine B (red);

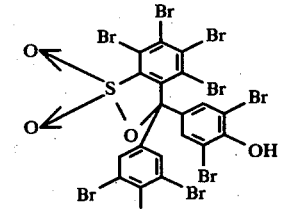

(6) Tetra bromo phenol blue:

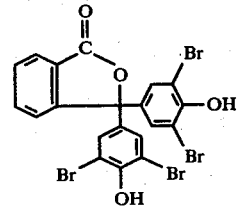

(7) Tetrabromophenolphthalein: 3,3-Bis-(3,5-dibromo-4-hydroxy-phenyl)-1(3H)-isobenzofuranone

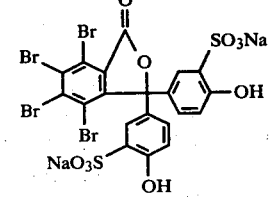

(8) Sulfobromophthalein sodium (BSP): 5,5'-(4,5,6,7-tetrabromo-3-oxo-1(3H)-isobenzofuranylidene)

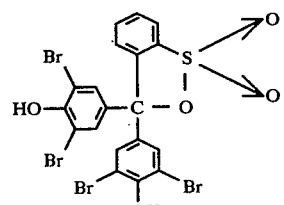

TABLE I-continued

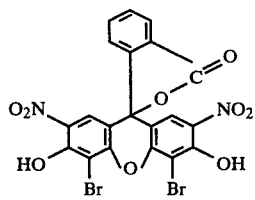

bis[2-hydroxybenzenesulfonic acid] disodium salt (9)

Eosine I bluish: 4',5'-dibromo-3',6'-dihydroxy-2',7'-dinitro spiro[isobenzofuran-1(3H),9'[9H]xanthen]-3-one disodium salt

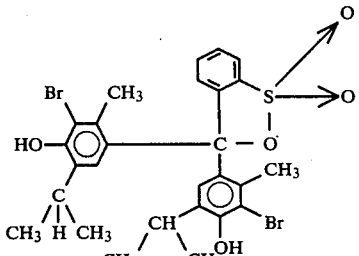

(10)

Bromthymol Blue: 4,4'-(3H-2,1-benzoxathiol-3-ylidene)bis[2-bromo-3-methyl-6-(1-methylethyl)phenol]S,S-dioxide

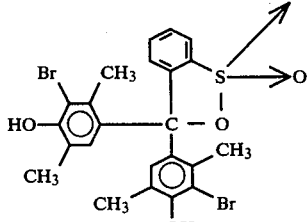

(11)

Bromoxylenol Blue:

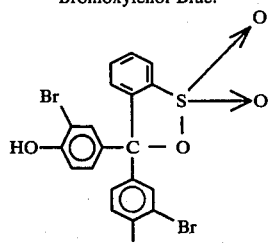

(12)

Bromophenol Red:

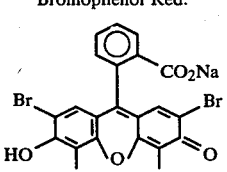

(13)

Eosine Yellowish: 2',4',5',7'-tetrabromofluorescein

Preferably the reaction is carried out in an inert organic reaction medium, such as glacial acetic acid, in which the dye precursor compound is placed. The reactant bromine, i.e., $^{76}Br_2$, $^{77}Br_2$ or $^{82}Br_2$, is in either the gaseous or liquid state. It is preferably introduced into the reaction mixture in the gaseous state through some kind of gas dispersing means. Introduction of the reactant bromine gas in this manner effects sufficient agitation of the reaction mixture to avoid the necessity of any other kind of agitation, although this may, of course, be done if so desired. With respect to the bromine reactant, if $^{82}Br_2$ is chosen, it can be supplied directly as it is commercially available. Since $^{77}Br_2$ is not commercially available, it must be generated from $K^{77}Br$, in a manner such as is described by Slaunwhite and Neeley, Analytical Biochemistry, Vol. 5, page 133 (1963).

The reaction vessel containing the reaction mixture is disposed in a leaded fume hood and can be heated in any desired manner, but it is preferred to do this by immersion in an oil bath maintained at the desired reaction temperature. The heating is carried out at a temperature and for a time period sufficient to effect the desired bromination reaction. The temperature may be in the range of from about 110° C. to 125° C. Thetime of reaction may be in the range of from about 4 hours to 12 hours. Since HBr is formed as a by-product of the bromination reaction, it is vented from the reaction vessel, and passed serially through two NaOH containing traps wherein it is neutralized to form NaBr. Since this is radioactive, it can be disposed of in any suitable and approved manner.

After the reaction has been completed, the reaction vessel is flushed with nitrogen gas to remove HBr, and the solvent is removed by evaporation. The reaction vessel is then removed from the oil bath, preferably by the use of tongs, but maintained disposed in the leaded fume hood. While still in the hood, the contents of the reaction vessel are removed, and then subjected to a separation procedure such as selective extraction in order to recover the dye compound labelled with the radioactive bromine. Thereafter, and while still being maintained within the leaded fume hood, the dye compound is subjected to a purification procedure, e.g., column chromatography.

As stated above, FIG. 2 illustrates an apparatus arrangement suitable for carrying out the process set forth in the flow sheet of FIG. 1.

If $^{77}Br_2$ is employed in the apparatus of FIG. 2, then the $^{77}Br_2$ source consists of a $^{77}Br_2$ generator which converts $^{77}Br^-$ to $^{77}Br_2$. This has been previously described by Slaunwhite and Neeley, utilizing manganese dioxide as the oxidizing agent. The $^{77}Br_2$ is distilled into the reaction mixture and then the reaction vessel is sealed.

The following Examples are given merely as illustrative of the present invention and are not to be considered as limiting.

EXAMPLES OF THE INVENTION

Example 1

Synthesis of Bromphenol Blue Labelled With $^{77}Br$

Starting Material:

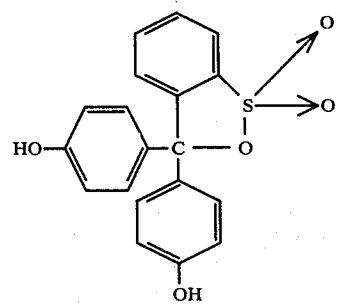

The above starting compound and glacial acetic acid were added to a reaction vessel disposed in an oil bath, all of which were placed in a leaded fume hood. Thereafter, $^{77}Br_2$ in gaseous form was supplied to the reaction vessel. Then the reaction vessel was heated in the oil bath at 123° C. and the reaction was completed in about 4–24 hours.

After the reaction was completed, the reaction vessel was flushed with nitrogen gas to remove HBr, and the solvent was removed by evaporation. The reaction vessel was then removed from the oil bath, preferably by the use of tongs. Thereafter, and while still in the leaded fume hood, the contents of the reaction vessel were removed and selectively extracted to recover the desired product, i.e., the dye compound labelled with radioactive bromine, which was then purified by column chromotography. The product had the formula:

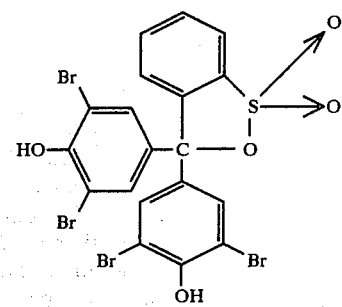

This product was diluted with an aqueous buffer, and then stored in a lead container in the leaded fume hood in which it had been prepared.

Examples 2–13

The procedure set forth in Example 1 above was carried out, but employing as the starting material in each example, the immediate precursor compound containing no bromine but otherwise corresponding to the compounds listed as entries 2–13 Table I above. The reaction temperature and time of reaction were varied as required to obtain the desired product. The products obtained by these Examples 2–13 correspond to entries 2 to 13 in said Table I above.

MODIFICATIONS AND EQUIVALENTS

With respect to the dyes which are labelled with radioactive $^{76}Br$, $^{77}Br$ or $^{82}Br$, this invention is not limited to the specific dyes disclosed in the foregoing description. Thus, these specific dyes can be modified so that the bromine substituents can be at positions other than those specifically shown.

In addition, the dyes which are labelled with radioactive $^{76}Br$, $^{77}Br$ or $^{82}Br$ and which can be prepared by this invention are not limited to the classes of dyes shown in the foregoing description. Any known bromine-containing dye which is excreted to a large extent in the bile of a number of animal species is suitable if it is labelled with $^{76}Br$, $^{77}Br$ or $^{82}Br$, i.e., if the non-radioactive Br substituents are replaced by $^{76}Br$, $^{77}Br$ or $^{82}Br$ in part or in whole.

Finally, with respect to the dyes which are taught as labelled with radioactive $^{76}Br$, $^{77}Br$ or $^{82}Br$, this invention is not limited to the use of these three bromine isotopes. Any gamma-emitting isotope of bromine can be employed.

Moreover, although the flow diagram of FIG. 1 shows the reaction as being carried out in glacial acetic acid, there are many other inert reaction media which are suitable for this purpose. Examples thereof are lactic acid and propionic acid. In general, any acidic media in which the brominating agent and the precursor dye are soluble are suitable.

The flow diagram of FIG. 1 shows the reaction vessel being heated by immersion in an oil bath. Many other variants for such heating are available. For example, the reaction vessel can be jacketed, and a heat exchange liquid circulated therethrough. An alternative is the use of an electrically heated resistance wire wrapped around the exterior of the reaction vessel.

Next, the flow diagram of FIG. 1 teaches separation of the dye compound from the reaction mixture by evaporation of the reaction medium followed by selective extraction. This, of course, could be varied in many ways. For example, chromatographic techniques such as tlc and hplc, etc., are suitable.

Further, the flow diagram of FIG. 1 shows purification of the dye compound by column chromatography. Other procedures such as recrystallization, etc. are also suitable.

An alternative synthesis in which the starting material is the relatively inexpensive bromide anion ($^{76}Br^-$, $^{77}Br^-$, or $^{82}Br^-$) can be carried out. Specifically, a solution of the alkali salt of the appropriate isotopic bromide is added to an acidic solution of potassium bromate and the specific precursor dye. The resultant solution is extracted into benzene, and the extract worked up in a similar fashion to that described in Example 1 for the reaction mixture containing the labelled dye.

USE IN PATIENTS

The selected dye labelled with a gamma-emitting isotope of bromine, i.e., $^{76}Br$, $^{77}Br$ or $^{82}Br$, is injected intravenously into the patient. Following injection, the liver and biliary system are monitored using equipment which maps radioisotope distribution within the human body. Digital data can also be stored on magnetic tape, allowing computer processing to provide graphs showing activity variations with time in selected areas of the scan (liver, gallbladder, intestine, etc.).

Distribution studies of the labelled dye after intravenous injection show initial rapid clearance of the radioactivity from the blood, specifically by the liver, with subsequent, almost complete, excretion into the biliary tract. Stated otherwise, the labelled dye of this invention rapidly accumulates in the liver, and then is excreted from the liver to the biliary tract, so as to be useful for hepatic-biliary morphology and function studies.

The monitoring equipment to be employed is well known in the art. One type of monitoring equipment found to be particularly useful for the purposes of this invention is of the scanning type, i.e., the scanning head thereof is caused to trace an interlaced pattern which covers the area of the body which is of interest. One example of such equipment is that described in U.S. Pat. No. 3,509,341 to Hindel et al, issued Apr. 28, 1970. In this system there is provision for storing the scanning data on magnetic tape for any desired use.

If it is desired to use monitoring equipment of the camera type, i.e., stationary with respect to the human body, but which can be employed to monitor specific areas of the human body, then U.S. Pat. No. 3,983,394 to Martone et al, issued Sept. 28, 1976, is of particular interest. In this system there is provided window generating circuitry for defining a window in the detector field of view, and for gating to an output an indication of only those stimuli occurring within the window. This enables a very precise monitoring of a specific organ in the human body to be carried out.

The system described in U.S. Pat. No. 3,308,438 to Spergel et al, issued Mar. 7, 1967, is of particular interest with respect to the dynamic imaging studies referred to above. In this system radiation data are accumulated for a short period of time and then destructively read out of the memory and displayed on a cathode ray tube at selected rates. Such a system has numerous advantages, e.g., an immediate and accurate presentation of the monitored subject may be observed in detail as the actual events occur, or the system may be employed to provide permanent records for subsequent study as desired.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A process for imaging the liver or biliary tract of a patient comprising the steps of:
   intravenously injecting the patient with a dye labelled with a gamma-emitting isotope of bromine; and then scintigraphically imaging the liver or biliary tract of the patient.

2. A process as recited in claim 1 in which the gamma-emitting isotope of bromine is selected from the group consisting of $^{76}Br$, $^{77}Br$ and $^{82}Br$.

3. A process for serially imaging the liver and biliary tract of a patient comprising the steps of:
   intravenously injecting the patient with a dye labelled with a gamma-emitting isotope of bromine; and then scintigraphically imaging the liver and biliary tract to follow the movement of radioactivity into the liver and then from it through the biliary tract.

4. A process as recited in claim 4 in which the gamma-emitting isotope of bromine is selected from the group consisting of $^{76}Br$, $^{77}Br$ and $^{82}Br$.

5. A process for imaging the liver or biliary tract of a patient comprising the steps of:
   intravenously injecting the patient with a dye selected from the group consisting of triarylmethane dyes and the phthalein subclass of the class of xanthene dyes, said dye being labelled with a gamma-emitting isotope of bromine; and then scintigraphically imaging the liver or biliary tract of the patient.

6. A process as recited in claim 5 in which the gamma-emitting isotope of bromine is selected from the group consisting of $^{76}Br$, $^{77}Br$ and $^{82}Br$.

7. A process as recited in claim 5 in which the gamma-emitting isotope of bromine is $^{77}Br$.

8. A process as recited in claim 5 in which the dye labelled with a gamma-emitting isotope of bromine has the structural formula:

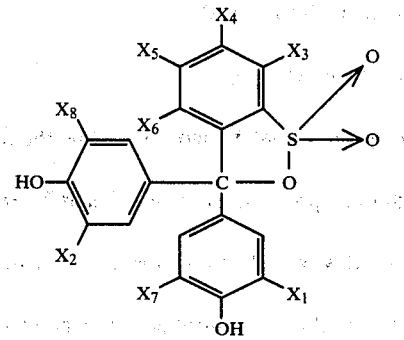

wherein
$X_1$ is Br or $CH_3$,
$X_2$ is Br or $CH_3$,
$X_{3-6}$ is Br or H,
$X_7$ is Br or H, and
$X_8$ is Br or H,
with the proviso that $X_1$ and $X_2$ must be the same; with the additional proviso that when $X_1$ and $X_2$ are Br, then $X_{3-6}$ is H, and $X_7$ and $X_8$ are Br or H; with the further proviso that when $X_1$ and $X_2$ are $CH_3$, then $X_{3-6}$ is H and $X_7$ and $X_8$ are Br; with the still further proviso that when $X_{3-6}$ is Br, then $X_1$, $X_2$, $X_7$ and $X_8$ are Br; and with the final proviso that the Br substituents are gamma-emitting isotopes.

9. A process as recited in claim 8 in which the dye labelled with a gamma-emitting isotope of bromine has the structural formula:

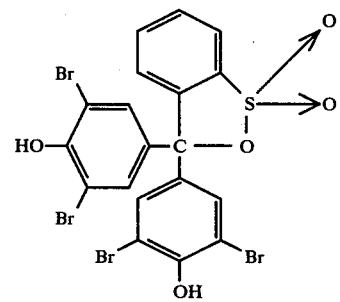

in which the Br substituents are $^{77}Br$.

10. A process as recited in claim 5 in which the dye labelled with a gamma-emitting isotope of bromine has the structural formula:

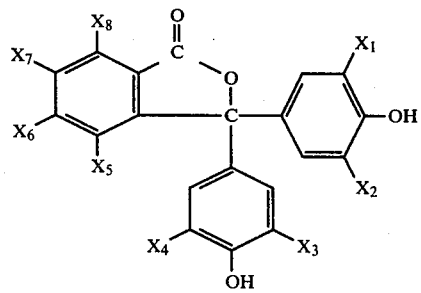

wherein
$X_1$ is Br or $SO_3Na$,
$X_2$ is Br or H,
$X_3$ is Br or H, $X_4$ is Br or $SO_3Na$, and $X_{5-8}$ is Br or H, with the proviso that $X_1$ and $X_4$ must be the same; with the additional proviso that when $X_1$ and $X_4$ are $SO_3Na$, then $X_2$ and $X_3$ are H and $X_{5-8}$ is Br; and with the final proviso that the Br substituents are gamma-emitting isotopes.

11. A process as recited in claim 5 in which the dye labelled with a gamma-emitting isotope of bromine has the structural formula:

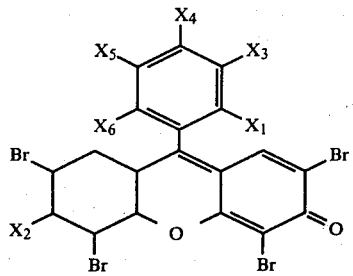

wherein
$X_1$ is $CO_2CH_2CH_3$ or $CO_2Na$,
$X_2$ is OH or NaO, and
$X_{3-6}$ is Cl or H,
with the proviso that when $X_1$ is $CO_2CH_2CH_3$, then $X_2$ is OH and $X_{3-6}$ is H; with the additional proviso that when $X_1$ is $CO_2Na$ and $X_{3-6}$ is Cl, then $X_2$ is NaO; with the further proviso that when $X_1$ is $CO_2Na$ and $X_{3-6}$ is H, then $X_2$ is OH; and with the final proviso that the Br substituents are gamma-emitting isotopes.

* * * * *